(12) United States Patent
Teh et al.

(10) Patent No.: US 11,747,423 B2
(45) Date of Patent: Sep. 5, 2023

(54) METHOD OF PERFORMING DIFFUSION WEIGHTED MAGNETIC RESONANCE MEASUREMENTS

(71) Applicant: Random Walk Imaging AB, Åkarp (SE)

(72) Inventors: Irvin Teh, Leeds (GB); Samo Lasic, Lund (SE); Markus Nilsson, Oxie (SE); Filip Szczepankiewicz, Lund (SE)

(73) Assignee: Random Walk Imaging AB, Åkarp (SE)

( * ) Notice: Subject to any disclaimer, the term of this patent is extended or adjusted under 35 U.S.C. 154(b) by 0 days.

(21) Appl. No.: 17/594,685

(22) PCT Filed: Apr. 24, 2020

(86) PCT No.: PCT/SE2020/050414
§ 371 (c)(1),
(2) Date: Oct. 26, 2021

(87) PCT Pub. No.: WO2020/218966
PCT Pub. Date: Oct. 29, 2020

(65) Prior Publication Data
US 2022/0221542 A1    Jul. 14, 2022

(30) Foreign Application Priority Data
Apr. 26, 2019    (SE) .................................... 1950507-2

(51) Int. Cl.
*G01R 33/563*    (2006.01)
*A61B 5/055*    (2006.01)
*G01R 33/565*    (2006.01)

(52) U.S. Cl.
CPC ........ *G01R 33/56341* (2013.01); *A61B 5/055* (2013.01); *G01R 33/56509* (2013.01); *G06T 2207/10092* (2013.01)

(58) Field of Classification Search
None
See application file for complete search history.

(56) References Cited

U.S. PATENT DOCUMENTS

2010/0277169 A1    11/2010   Feiweier
2013/0187649 A1    7/2013    Bhat et al.
(Continued)

FOREIGN PATENT DOCUMENTS

WO    2013025487 A1    2/2013
WO    2015119569 A1    8/2015
(Continued)

OTHER PUBLICATIONS

International Search Report and Written Opinion, International Application No. PCT/SE2020/050414, dated May 5, 2020, 12 pages.
(Continued)

*Primary Examiner* — Rodney E Fuller
(74) *Attorney, Agent, or Firm* — CHRISTENSEN O'CONNOR JOHNSON KINDNESS PLLC

(57) ABSTRACT

Inventive technology is directed to diffusion weighted magnetic resonance measurements. In an embodiment, a method for performing a diffusion weighted magnetic resonance measurement on a sample includes operating a magnetic resonance scanner to apply a diffusion encoding sequence to the sample. The method also includes operating the magnetic resonance scanner to acquire from the sample one or more echo signals. The diffusion encoding sequence includes a diffusion encoding time-dependent magnetic field gradient g(t) with non-zero components $g_i(t)$ along at least
(Continued)

two orthogonal directions y and z, and a b-tensor having at least two non-zero eigenvalues, the magnetic field gradient comprising a first and subsequent second encoding block.

14 Claims, 8 Drawing Sheets

(56) References Cited

U.S. PATENT DOCUMENTS

| | | | |
|---|---|---|---|
| 2016/0291113 | A1 | 10/2016 | Stemmer |
| 2017/0234956 | A1 | 8/2017 | Feiweier |
| 2018/0348325 | A1 | 12/2018 | Feiweier et al. |
| 2019/0004137 | A1 | 1/2019 | Harris et al. |
| 2020/0284865 | A1* | 9/2020 | Szczepankiewicz ........... G01R 33/5617 |

FOREIGN PATENT DOCUMENTS

| | | |
|---|---|---|
| WO | 2017116300 A1 | 7/2017 |
| WO | 2017132180 A1 | 8/2017 |
| WO | 2018088954 A1 | 5/2018 |
| WO | 2018088955 A1 | 5/2018 |
| WO | 2019050462 A1 | 3/2019 |

OTHER PUBLICATIONS

Westin et al., "Q-space trajectory imaging for multidimensional diffusion MRI of the human brain," NeuroImage, vol. 135, Jul. 2016, pp. 345-362.
Topgaard, "Multidimensional diffusion MRI," Journal of Magnetic Resonance, vol. 275, Feb. 2017, pp. 98-113.
Lampinen et al., "Neurite density imaging versus imaging of microscopic anisotropy in diffusion MRI: A model comparison using spherical tensor encoding," Neuroimage, vol. 147, Feb. 2017, pp. 517-531.
Nilsson et al., "Imaging brain tumour microstructure," NeuroImage, vol. 182, Nov. 2018, pp. 232-250.
Szczepankiewicz et al., "Tensor-valued diffusion encoding fordiffusional variance decomposition (DIVIDE): Technical feasibility in clinical MRI systems," PlosOne, nr.3, vol. 14., Mar. 2019, pp. 1-20.
Topgaard, "Diffusion tensor distribution imaging," NMR in biomedicine, nr.5, vol. 32., Feb. 2019, pp. 1-12.
Aliotta et al., "Convex optimized diffusion encoding (CODE) gradient waveforms for minimum for echo time and bulk motion-compensated diffusion-weighted MRI," Magnetic Resonance in Medicine, nr.2, vol. 77, Feb. 2017, pp. 717-729.
Afzali et al., "Comparison of different tensor encoding combinations in microstructural parameter estimation," 2019 IEEE 16th International Symposium on Biomedical Imaging, Apr. 2019, pp. 1471-1474.
Gumus et al. "Prevention of Motion-Induced Signal Loss in Diffusion-Weighted Echo-Planar Imaging by Dynamic Restoration of Gradient Moments," Magnetic Resonance in Medicine, nr.6, vol. 71, Jun. 2014, pp. 2006-2013.
Moulin et al. "Effect of flow-encoding strength on intravoxel incoherent motion in the liver," Magnetic Resonance in Medicine, nr.3, vol. 81, Sep. 2018, pp. 1521-1533.
Szczepankiewicz, et al., "Maxwell-compensated design of asymmetric gradient waveforms for tensor-valued diffusion encoding," Magnetic Resonance in Medicine, vol. 82, first published May 31, 2019, arXiv, 24 pages.
Welsh et al., "Higher-Order Motion-Compensation for In Vivo Cardiac Diffusion Tensor Imaging in Rats," IEEE Transactions on Medical Imaging, nr.9, vol. 34, Sep. 2015, pp. 1843-1853.
Extended European Search Report dated Dec. 21, 2022, issued in corresponding European Application No. 20795044, filed Apr. 24, 2020, 7 pages.
N. Moutal et al., "Probing Surface-to-Volume Ratio of an Anisotropic Medium by Diffusion NMR with General Gradient Encoding," in IEEE Transactions on Medical Imaging, vol. 38, No. 11, pp. 2507-2522, Nov. 2019, doi: 10.1109/TMI.2019.2902957.
S. Lasic et al., "Motion-compensated b-tensor encoding for in vivo cardiac diffusion-weighted imaging", NMR in Biomedicine, 2020, https://doi.org/10.1002/nbm.4213, Published by John Wiley & Sons Ltd.

* cited by examiner

METHOD OF PERFORMING DIFFUSION WEIGHTED MAGNETIC RESONANCE MEASUREMENTS

CROSS-REFERENCES TO RELATED APPLICATIONS

This application is a National Stage of International Application No. PCT/SE2020/050414 filed Apr. 24, 2020, which claims the benefit of Swedish Application No. 1950507, filed Apr. 26, 2019, now Swedish Patent No. 543292, issued Nov. 17, 2020, the disclosures of which are incorporated herein in their entirety.

TECHNICAL FIELD

The present inventive concept relates to a method of performing diffusion weighted magnetic resonance measurements on a sample.

BACKGROUND

Diffusion-weighted magnetic resonance imaging (dMRI) can be used to probe tissue microstructure and has both scientific and clinical applications. Diffusion encoding magnetic field gradients allow MR measurements to be sensitized for diffusion, which in turn can be used to infer information about tissue microstructure, anisotropy, shape and size of the constituent compartments, which may represent confinements/restrictions for diffusion of spin-bearing particles.

Recent developments in so-called b-tensor encoding have demonstrated that greater specificity to microstructural features can be recalled from imaging data. In particular b-tensor encoding allows for encoding schemes extending beyond linear/directional diffusion encoding (1D) traditionally used in e.g. diffusion tensor imaging (DTI), to multidimensional diffusion encoding including planar (2D) and ellipsoidal and spherical (3D) encoding. As disclosed for instance in "Measurement Tensors in Diffusion MRI: Generalizing the Concept of Diffusion Encoding" (Westin C-F, Szczepankiewicz F, Pasternak O, et al., *Med Image Comput Comput Assist Interv* 2014; 17:209-216) such schemes can be described by diffusion encoding/weighting tensors with more than one non-zero eigenvalues and can, to various degrees, reduce or eliminate the confounding effect of orientation dispersion and provide sensitivity specific to compartment (diffusion tensor) anisotropy As one example, the approach disclosed in "Microanisotropy imaging: quantification of microscopic diffusion anisotropy and orientational order parameter by diffusion MRI with magic-angle spinning of the q-vector". (Lasič S, Szczepankiewicz F, Eriksson S, Nilsson M, Topgaard D, *Front Phys* 2014; 2:1-14), which maximizes the separation between the effects of compartment (diffusion tensor) anisotropy and orientation dispersion, combines directional (1D) and isotropic (3D) encoding to quantify microscopic fractional anisotropy (μFA).

Current multidimensional diffusion encoding methods however typically assume there is no bulk motion of the sample during measurement. Bulk motion of the sample may result in signal drop out as well as signal and image artefacts. In some applications bulk motion of the sample cannot be avoided, such as when the object of interest is the tissue of a moving organ of a patient, for instance a heart. For this reason, dMRI-based analysis of microstructure of tissue of moving organs using current b-tensor encoding schemes is presently challenging.

SUMMARY OF THE INVENTIVE CONCEPT

An objective of the present inventive concept is to provide a method which allows precise diffusion weighted magnetic resonance measurements on a sample, even in presence of bulk motion of the sample. Further and alternative objectives may be understood from the following.

According to an aspect of the present inventive concept, there is provided a method for performing a diffusion weighted magnetic resonance measurement on a sample, the method comprising:

operating a magnetic resonance scanner to apply a diffusion encoding sequence to the sample; and operating the magnetic resonance scanner to acquire from the sample one or more echo signals;

wherein the diffusion encoding sequence comprises a diffusion encoding time-dependent magnetic field gradient $g(t)$ with non-zero components $g_i(t)$ along at least two orthogonal directions y and z, and a b-tensor having at least two non-zero eigenvalues, the magnetic field gradient comprising a first and subsequent second encoding block, wherein an n-th order gradient moment magnitude along direction $l \in (y,z)$ is given by $|M_{nl}(t)| = |\int_0^t g_l(t') t'^n dt'|$, and the first encoding block is adapted to yield, at an end of the first encoding block:

along said direction y, $|M_{ny}(t)| \le T_n$ for each $0 \le n \le m$, where $T_n$ is a predetermined n-th order threshold, and along said direction z, $|M_{nz}(t)| \le T_n$ for each $0 \le n \le m-1$ and $|M_{nz}(t)| > T_n$ for n=m; and the second encoding block is adapted to yield, at an end of the second encoding block:

along each one of said directions $l \in (y, z)$: $|M_{nl}(t)| \le T_n$ for each $0 \le n \le m$, wherein m is an integer order equal to or greater than 1.

According to the inventive method for diffusion weighted magnetic resonance measurement, multidimensional diffusion encoding sequences may be adapted to present a reduced sensitivity to (i.e. compensation for) e.g. velocity (if m=1); or velocity and acceleration (if m=2). As will be further described below, the method allows for planar diffusion encoding (2D) as well as ellipsoidal and spherical diffusion encoding (3D).

The lower the value of the thresholds $T_n$, the greater the degree of motion compensation may be achieved. From the perspective of maximizing the degree of motion compensation it may be preferable that the gradient moment magnitudes along each direction assume a zero value, i.e. are "nulled", at the end of the second encoding block (corresponding to $T_n=0$ for each order $0 \le n \le m$). However, it is contemplated that a less strict motion compensation in some instances may be acceptable, e.g. in view of other requirements on the magnetic field gradient g(t). That is, the actual threshold values may be selected depending on the details of each measurement, such that a desired degree of motion compensation is achieved.

As realized by the inventors, a greater number of oscillations of the magnetic field gradient g(t) allows nulling of higher order gradient moments. However, a greater number of oscillations increases the demands on the magnetic resonance scanner. Accordingly, providing motion compensation along each direction in a single encoding block may not be easily attainable, especially in combination with multidimensional diffusion encoding which on its own may be hardware demanding. The inventive method therefore provides two encoding blocks and requires the m-th order gradient moment magnitude to meet/fall below the threshold $T_m$ along one of the directions (i.e. the y direction), but allows the m-th order gradient moment magnitude to exceed the threshold $T_m$ along the other direction (i.e. the z direction). Thereby, motion compensated multidimensional diffusion encoding may be implemented on a broader range of magnetic resonance scanners.

When referred to herein, the magnetic field gradient g(t) refers to the effective magnetic field gradient unless indicated otherwise. Hence g(t) represents the gradient waveform vector accounting for the spin-dephasing direction after application of an arbitrary number of radio frequency (RF) pulses forming part of the diffusion encoding sequence, such as refocusing pulses.

The n-th order gradient moment along a direction $l \in (y, z)$ is given by $M_{nl}(t) = \int_0^t g_l(t') t'^n dt'$. This definition of the n-th order gradient moment applies also in the case of non-zero components $g_l(t)$ along three orthogonal directions $l \in (x,y,z)$.

Accordingly, the n-th order gradient moment vector is given by $M_n(t) = \int_0^t g(t') t'^n dt'$.

The 0-th order gradient moment vector $$M_0(t) = \frac{1}{\gamma} q(t)$$

where q(t) is the dephasing vector $q(t) = \gamma \int_0^t g(t') dt'$ and $\gamma$ is the gyromagnetic ratio.

The tensor representation b, or shorter the "b-tensor", of the (effective) magnetic field gradient g(t) is given by $b = \gamma^2 \int_0^{\tau_E} M_0(t) \otimes M_0(t) dt$ where $\otimes$ represents the tensor product and $\tau_E$ represents the total encoding time extending between t=0 and t=$\tau_E$, equivalent to the echo time for a spin echo measurement.

References to directions or axes, such as x, y and z, should be understood as mere labels and should not be interpreted as references to particular axes of gradient coil channels of the scanner, unless indicated otherwise.

The integer order m referred to above may be a predetermined value, selected depending on which orders of motion should be compensated for. In some embodiments, m may be equal to 1. This allows for velocity compensation. In some embodiments, m may be equal to 2. This allows for velocity and acceleration compensation. In some embodiments, m may be greater than 2. This allows for velocity and acceleration compensation as well as compensation for higher order motion.

According to some embodiments the magnetic field gradient g(t) is adapted to present:

between a start of the first encoding block and the end of the first encoding block: m+1 zero crossings along said direction y and m zero crossings along said direction z, and between a start of the second encoding block and the end of the second encoding block: m+1 zero crossings along said direction y and m zero crossings along said direction z.

Adapting g(t) to present m+1 zero crossings along a direction in each encoding block allows motion compensation up to order m along said direction. This will be shown more rigorously in the below. Increasing the number of zero crossings beyond m+1 (i.e. increasing the number of gradient oscillations) is possible however imposes higher demands on the scanner and reduces the efficiency of diffusion-weighting.

Providing $g_l(t)$ with m+1 zero crossings allows for a subdivision of $g_l(t)$ into m+2 sub-intervals in each encoding block, wherein $g_l(t)=0$ at the start and end of each sub-interval.

The first and second encoding blocks may both be of a duration $\tau_B$ and begin at time $t_{B1}$ and $t_{B2}$, respectively, and be such that:

$$g_y(t_{B1}+t') = \pm g_y(t_{B2}+t'), \text{ and}$$

$$g_z(t_{B1}+t') = -g_z(t_{B2}+t')$$

for $0 \leq t' \leq \tau_B$.

As realized by the inventors, reversing the sign/polarity of the gradient component $g_z(t)$ during the second encoding block allows any residual m-th order gradient moment magnitude along the z direction to be reduced to become equal to or lower than the threshold $T_m$, i.e. such that $|M_{mz}(t)| \leq T_m$ along the z direction. The sign of the gradient component may be changed or un-changed along the y direction.

According to some embodiments the magnetic field gradient g(t) comprises a silent block between the first and second encoding blocks during which g(t) is zero, and wherein the diffusion encoding sequence further comprises at least one radio frequency pulse applied to the sample during the silent block.

For instance, a 180° refocusing pulse may be applied during the silent block. The echo signals may in that case be acquired as spin echoes at echo time $\tau_E$ or as part of a diffusion-prepared pulse sequence.

As mentioned above, both 2D and 3D diffusion encoding sequences are possible. 2D encoding may be achieved using a b-tensor having exactly two non-zero eigenvalues. 3D encoding may be achieved using a b-tensor having exactly three non-zero eigenvalues.

According to embodiments wherein the b-tensor has exactly three non-zero eigenvalues, the magnetic field gradient g(t) may present non-zero components $g_l(t)$ along three orthogonal directions x, y and z, and wherein:

the first encoding block is further adapted to yield, at the end of the first encoding block:

along said direction x, $|M_{nx}(t)| \leq T_n$ for each $0 \leq n \leq m$, and the second encoding block is further adapted to yield, at the end of the second encoding block:

along said direction x: $|M_{nx}(t)| \leq T_n$ for each $0 \leq n \leq m$.

Accordingly, the thresholds $T_n$ for each order $0 \leq n \leq m$ are enforced along the two directions x, y during the first and second encoding blocks, but only for orders $0 \leq n \leq m-1$ along the direction z in the first encoding block. This approach allows an in principle arbitrary shape of the b-tensor (e.g. prolate, oblate, spherical) while allowing motion compensation up to order m.

The magnetic field gradient g(t) may be adapted to present:

between a start of the first encoding block and the end of the first encoding block: m+1 zero crossings along each of said directions x and y and m zero crossings along said direction z, and between a start of the second encoding block and the end of the second encoding block: m+1 zero crossings along each of said directions x and y and m zero crossings along said direction z.

The above-discussed advantages related to the number of zero crossings apply correspondingly to this case of 3D encoding.

The first and second encoding blocks may be of a duration $\tau_B$ and begin at time $t_{B1}$ and $t_{B2}$, respectively, and wherein $$g_x(t_{B1}+t')=g_x(t_{B2}+t'),$$

$$g_y(t_{B1}+t')=-g_y(t_{B2}+t'), \text{ and}$$

$$g_z(t_{B1}+t')=-g_z(t_{B2}+t'),$$

for $0 \leq t' \leq \tau_B$.

As discussed above, reversing the sign/polarity of the gradient component $g_z(t)$ during the second encoding block allows any residual m-th order gradient moment magnitude along the z direction to be reduced to become equal to or lower than the threshold $T_m$, i.e. such that $|M_{mI}(t)| \leq T_m$ along the z direction. Meanwhile, reversing the sign only one of the other two directions allows 3D encoding to be obtained.

A trajectory of a dephasing vector $q(t)=\gamma\int_0^t g(t')dt'$ may be confined to two orthogonal planes during the magnetic field gradient $g(t)$. Restricting the trajectory of the dephasing vector to two orthogonal planes may improve diffusion-weighting efficiency in the design of the magnetic field gradient $g(t)$ to achieve the desired motion compensation.

As mentioned above, the present approach allows an in principle arbitrary shape of the b-tensor. It is envisaged that the motion compensation may be combined with isotropic diffusion encoding in the sample.

According to some embodiments the sample is arranged in a static magnetic field $B_0=(0, 0, B_0)$ oriented along said direction z, and wherein the magnetic field gradient $g(t)$ is oriented with respect to static magnetic field such that $$K = \frac{\gamma}{2\pi} \int_0^{\tau_E} h(t')G_C(t')dt'$$

is zero, where:

$$G_C(t) = \frac{1}{4B_0} \begin{bmatrix} g_z^2(t) & 0 & -2g_x(t)g_z(t) \\ 0 & g_z^2(t) & -2g_y(t)g_z(t) \\ -2g_x(t)g_z(t) & -2g_y(t)g_z(t) & 4g_x^2(t)+4g_y^2(t) \end{bmatrix}.$$

As realized by the inventors, by applying the gradient vector $g(t)$ with a rotation minimizing K, allows reducing the effects of concomitant fields to a negligible level. The magnetic field gradient $g(t)$ may hence be referred to as "Maxwell compensated", so to speak. Hence, signal attenuation due to concomitant field gradients, which otherwise could produce measurement artefacts, may be mitigated or avoided without use of position dependent correction gradients.

The method may further comprise processing, by a processing device, data representing the one or more echo signals acquired from the sample to generate an image of the sample, such as a dMRI image.

The first and second encoding blocks of the magnetic field gradient $g(t)$ may each comprises trapezoidal pulses or sinusoidal pulses. More generally, each encoding block may comprise a combination of trapezoidal and sinusoidal pulses.

As noted above, each $T_n$ may be a zero-threshold, i.e. equal to zero. In such a case, any statement herein of $|M_{ny}(t)| \leq T_n$ may be construed as $|M_{ny}(t)|$ being zero or nulled. Conversely, any statement herein of $|M_{ny}(t)| > T_n$ may be construed as $|M_{ny}(t)|$ being greater than zero, i.e. not nulled.

According to embodiments wherein m is equal to or greater than 1, $T_1$ may be 1.20E-5, more preferably 1.18E-5, or even or more preferably 1.17E-5 (with unit $T \cdot s^2 \cdot m^{-1}$). According to embodiments wherein m is equal to or greater than 2, $T_2$ may be 4.8E-7, more preferably 4.7E-7, even more preferably 4.6E-7 (with unit $T \cdot s^3 \cdot m^{-1}$). $T_0$ may for any value of m be 1.20E-2, more preferably 1.18E-2, even more preferably 1.17E-2 (with unit $T \cdot s \cdot m^{-1}$). These threshold values may provide a usable degree of motion compensation for various applications, such as wherein the sample is a heart or other moving organ of a patient.

BRIEF DESCRIPTION OF THE DRAWINGS

The above, as well as additional objects, features and advantages of the present inventive concept, will be better understood through the following illustrative and non-limiting detailed description of preferred embodiments of the present inventive concept, with reference to the appended drawings. In the drawings like reference numerals will be used for like elements unless stated otherwise.

DETAILED DESCRIPTION

In diffusion weighted magnetic resonance measurement techniques, such as dMRI, the microstructure of a sample, such as tissue, may be probed via the diffusion of spin-bearing particles in the sample, typically water molecules. The term "diffusion" implies a random or stochastic process of motion of the spin-bearing particles within the sample. Diffusion may include random molecular motion driven by thermal energy, chemical energy and/or concentration difference. Such diffusion is also known as self-diffusion. Diffusion may include dispersed or in-coherent or turbulent flow of molecules (i.e. flow with velocity dispersion) inside randomly oriented microstructures within the sample. Such diffusion is also known as "pseudo-diffusion". Hence, the effects of in-coherent flow within the sample may also give rise to signal attenuation due to the diffusion encoding magnetic field gradient sequences used in the present method. In the presence of bulk motion of the sample, as may be the case when performing measurements on a moving organ, such as a heart, the bulk motion may mask or distort the signal attenuation due to the actual diffusion.

In the following, diffusion encoding schemes allowing motion compensation to an arbitrary degree and up to an order of one or greater, and multidimensional diffusion encoding with b-tensors of arbitrary shape will be disclosed. The discussion and examples which follow will refer to 3D diffusion encoding (i.e. using a b-tensor having three non-zero eigenvalues) however as would be appreciated by the skilled person, they may with appropriate adaption be applied also to 2D diffusion encoding (i.e. using a b-tensor having only two non-zero eigenvalues).

Figure 1:
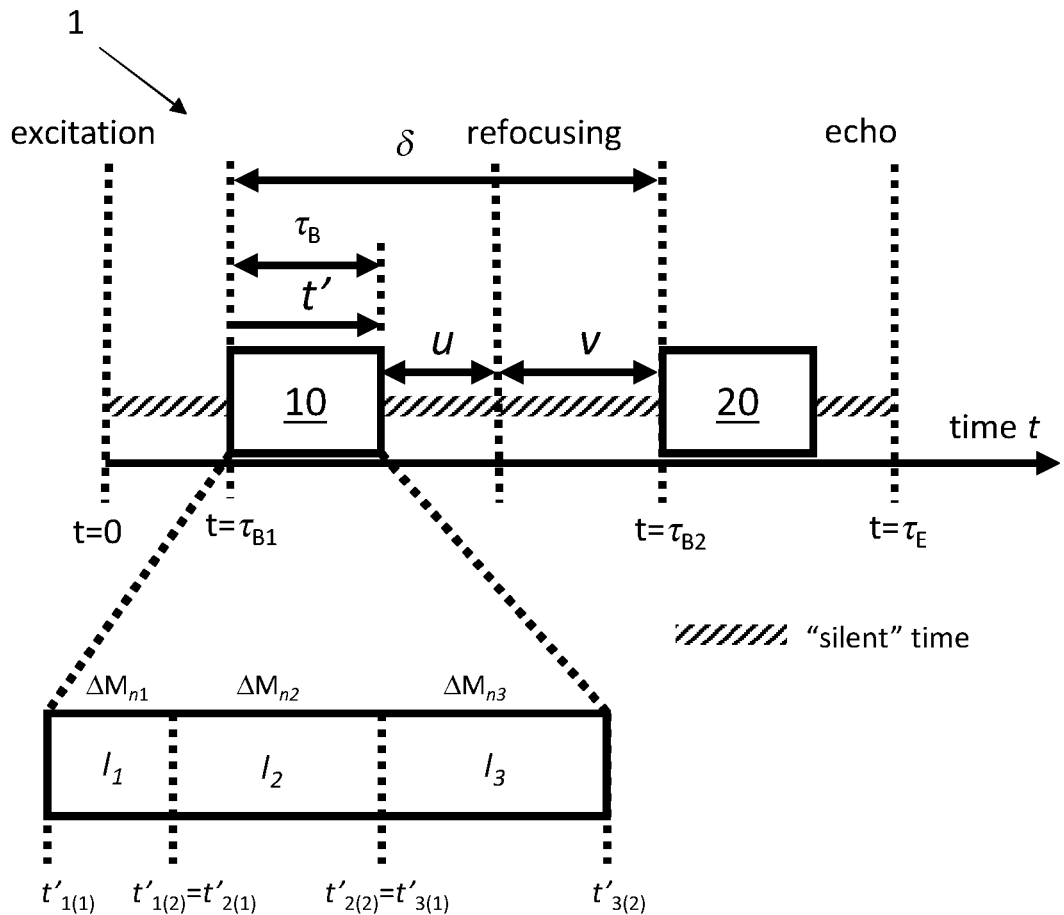
FIG. 1 schematically shows a format of an encoding sequence.

FIG. 1 is a schematic illustration of an encoding sequence 1 adapted for diffusion weighting, which may be implemented by a magnetic resonance scanner. The encoding sequence comprises a time-dependent magnetic field gradient, which in effective form may be represented as an effective gradient waveform vector $$[g(t)]_l = g_l(t), \quad (1)$$

where $l \in (x, y, z)$. The effective gradient wave form vector $g(t)$ takes into account the spin-dephasing direction after application of any number of refocusing RF pulses of the encoding sequence. The effective gradient wave form vector $g(t)$ is related to the laboratory gradient waveform vector through $$[g_{lab}(t)]_l = h(t) g_l(t), \quad (2)$$

where $l \in (x, y, z)$ and the sign function $h(t)$ assumes values of 1 or –1 for each encoding period separated by refocusing pulses or 90° pulse pairs, so that neighboring periods separated by a refocusing pulse have opposite signs. In the present disclosure, the terminologies "gradient waveform vector $g(t)$" and "magnetic field gradient $g(t)$" may be used as synonyms, and always referring to the effective form of the vector/gradient unless indicated otherwise.

The encoding sequence 1 begins at time t=0 with an RF excitation pulse and ends at the time of echo acquisition $t=\tau_E$. Hence, $\tau_E$ may represents the total encoding time.

The magnetic field gradient $g(t)$ of the encoding sequence 1 comprises a first encoding block 10 and a second encoding block 20. The diagonal pattern indicates "silent time" of the encoding sequence 1 during which the magnetic field gradient $g(t)$ is zero, i.e. absence of any diffusion encoding magnetic gradient. Accordingly, as indicated by FIG. 1, the encoding sequence 1 may comprise a silent block between the first and second encoding blocks 10, 20. The first encoding block 10 hence signifies a part of the magnetic field gradient $g(t)$ prior to the silent block while the second encoding block 20 signifies a part of the magnetic field gradient $g(t)$ after the silent block.

The first encoding block 10 starts at time $t=\tau_{B1}$, i.e. the first time the magnetic field gradient $g(t)$ becomes non-zero after the excitation pulse. The duration of the first encoding block 10 is $\tau_B$. The first encoding block 10 ends at time $t=\tau_{B1}+\tau_B$, i.e. the last time the magnetic field gradient $g(t)$ becomes zero prior to the silent block. The second encoding block 20 starts at time $t=\tau_{B2}$, i.e. the first time the magnetic field gradient $g(t)$ becomes non-zero after the silent block. The separation in time between the start of the first encoding block 10 and the start of the second encoding block 20 is given by $\delta$. The duration of the second encoding block 20 is $\tau_B$. The second encoding block 20 ends at time $t=\tau_{B2}+\tau_B$, i.e. the last time the magnetic field gradient $g(t)$ becomes zero prior to the end of the encoding sequence 1 $t=\tau_E$.

One or more RF pulses may be applied to the sample during the silent block, for example a single 180° refocusing RF pulse or a train of two or more 90° RF pulses. In FIG. 1, the parameter u denotes the time between the end of the first encoding block 10 and the start of the RF pulse(s) and the parameter and v denotes the time between the end of the RF pulse(s) and the start of the second encoding block 20. u and v may either be equal or different from each other. Encoding blocks can thus be applied symmetrically (u=v) or asymmetrically (u≠v) around the RF pulse(s).

Although FIG. 1 indicates a same duration $\tau_B$ of the first and second encoding blocks 10, 20 it is contemplated that the first and second encoding blocks also may be of different durations. Moreover, although FIG. 1 indicates presence of two encoding blocks, it is contemplated that the encoding sequence may comprise more than two encoding blocks, such as three, four or more encoding blocks. The following discussion is applicable also to such an extended encoding sequence provided the first and second encoding blocks 10, 20 represent the last consecutive pair of encoding blocks of the extended encoding sequence.

Based on the gradient waveform vector $g(t)$, a time-dependent n-th gradient moment vector may be defined as $$M_n(t) = \int_0^t g(t') t'^n dt'. \quad (3)$$

The evolution of $M_0(t)$ is proportional to the q-trajectory and may be referred to as such. The diffusion encoding tensor is given by $$b = \gamma^2 \int_0^{\tau_E} M_0(t) \otimes M_0(t) dt, \quad (4)$$

where $\otimes$ represents tensor product and $\gamma$ is gyromagnetic ratio.

For the purpose of the following analysis, a relative block time t' may be defined as the local time of each encoding block 10, 20, i.e. starting starting at t'=0 at the start of an encoding block and ending at $t'=\tau_B$ at the end of the encoding block.

Any encoding block may as shown in FIG. 1 be subdivided into v block sub-intervals $I_1, I_2, I_3$ etc. Let the i-th sub-interval $I_i$ start at the relative time $t'_{i(1)}$ and end at $t'_{i(2)}$, where $0 \leq t'_{i(1),(2)} \leq \tau_B$. The sub-interval duration is $\Delta t'_i = t'_{i(2)} - t'_{i(1)}$, so that $\sum_{i=1}^{v} \Delta t'_i = \tau_B$ and $t'_{i(1)} \leq t' \leq t'_{i(2)}$ for all $t' \in I_i$.

Let a component of vector $g(t)$ within each sub-interval $I_i$ of an encoding block 10, 20 be given by $C_i \tilde{f}_i(t \in I_i)$, where $C_i$ are positive or negative real constants and $\tilde{f}_i(t)$ are normalized waveforms, where $|\tilde{f}_i(t)| \leq 1$. The entire component of the effective gradient within a block is thus given by a piecewise function $f(t)$ defined for each sub-interval. A trivial condition for $f(t)$ to be continuous, is that $\tilde{f}=0$ at the beginning and end of each sub-interval. An increment of a component of the n-th gradient moment vector $M_n(t)$ within the i-th sub-interval $I_i$ is given by $$\Delta M_{ni} = C_i \Delta \tilde{M}_{ni}, \quad (5)$$

$$\Delta \tilde{M}_{ni} = \int_{t \in I_i} \tilde{f}_i(t) t^n dt. \quad (6)$$

The total increment of a component of $M_n(t)$ within an encoding block is zero when $$\Delta M_n = \sum_{i=1}^{v} \Delta M_{ni} = \sum_{i=1}^{v} C_i \Delta \tilde{M}_{ni} = 0. \quad (7)$$

Components of $M_n(t)$, i.e. $M_{nl}(t)$ $l \in (x, y, z)$, are nulled at $t=\tau_E$ either when $\Delta M_n = 0$ for each encoding block or when the sum of $\Delta M_n$ from all encoding blocks is zero. Let's first consider conditions for $\Delta M_n = 0$ in a single encoding block. We have v adjustable parameters to fulfill condition (7). We can now deduce what is the minimum required number of sub-intervals v to fulfill (7) for all moments up to n, i.e.

$$\Delta M_0 = 0, \Delta M_1 = 0, \ldots \Delta M_n = 0. \quad (8)$$

For the purpose of nulling moments, we can arbitrarily scale the entire waveform within an encoding block and thus set $C_1 = 1$ in (7), which leads to condition $$\Delta \tilde{M}_{n1} + \Sigma_{i=2}^{v} C_i \Delta \tilde{M}_{ni} = 0 \quad (9)$$

with v−1 adjustable parameters. The requirement (8) together with condition (9) can be formulated as a system of equations given by $$\Delta MC = 0, \quad (10)$$

where $\Delta M$ is an n by v matrix with elements $\Delta \tilde{M}_{ij}$ and C is a 1 by v vector $C = (1, C_2, C_3, \ldots, C_v)^T$ with v−1 free parameters. The critical case to solve for C is when v=n+2. For velocity compensation, n=1 and thus v=3. For velocity and acceleration compensation, n=2 and v=4. With $\tilde{f}_i = 0$ at the beginning and end of each sub-interval this may be expressed in terms of the number of zero crossings between the start and end of an encoding block, i.e. n+1. Hence, for velocity compensation, n=1 and thus the number of zero crossings becomes 2. For velocity and acceleration compensation, n=2 and the number of zero crossings becomes 3. In other words, designing a component $g_i(t)$ of the gradient waveform vector g(t) to present n+1 zero crossings (or equivalently n+2 sub-intervals) allows for (with proper scaling $C_i$ of $\tilde{f}_i(t)$, as may be determined using equation (10)) achieving a $\Delta M_n$ along the direction l with a magnitude/absolute value equal to or smaller than an arbitrarily small threshold $T_n$.

Let's now consider the case of multiple encoding blocks such as encoding blocks 10, 20 with onset times at $t_{B1}$, $t_{B2}$, respectively. Let's first examine the case of blocks of equal duration $\tau_B$. For any gradient vector component, to have all moments up to the n-th order nulled after the second block 20, we only need to fulfil condition (9) up to order n−1 in each of the encoding blocks 10, 20. For this we need to apply, in the second block 20, identical effective gradients but with opposite polarity compared to the first block 10. When the two blocks are not of equal duration, different scaling of the gradients in two blocks would be required. Assuming that moment increments of all degrees less then n are zero after the first block 10, inverting gradient polarity in the second block 20 inverts the sign of moment increment, and any residual moment after the first encoding block 10 can thus be cancelled by inverting gradient polarity in the second block 20. We can show that this is true for any effective gradient vector component $g_i(t)$, for which $$g_i(t_{B2}+t') = -g_i(t_{B1}+t'), \quad (11)$$

where $0 \leq t' \leq \tau_B$. The total gradient moment increment due to the first block is $$\Delta M_{n,B1} = \int_{t_{B1}}^{\tau_B+t_{B1}} g_i(t) t^n dt = \int_0^{\tau_B} g_i(t+t_{B1})(t+t_{B1})^n dt. \quad (12)$$

The total gradient moment increment due to the second block is $$\Delta M_{n,B2} = \int_{t_{B2}}^{\tau_B+t_{B2}} g_i(t) t^n dt = \int_0^{\tau_B} g_i(t+t_{B2})(t+t_{B2})^n dt. \quad (13)$$

Considering Eq. (11) in Eq. (13), we have $$\Delta M_{n,B2} = -\int_0^{\tau_B} g_i(t+t_{B1})(t+t_{B1}+\delta)^n dt, \quad (14)$$

where $\delta = t_{B2} - t_{B1}$. By expanding the second factor we get $$\Delta M_{n,B2} = -\sum_{m=0}^{n} \binom{n}{m} \delta^m \Delta M_{n-m,B1}, \quad (15)$$

where $$\binom{n}{m}$$

are binomial coefficients. If $\Delta M_{k,B1} = 0$ for all k<n, we have $$\Delta M_{n,B2} = -\Delta M_{n,B1} \quad (16)$$

and thus, the total moment $M_n = \Delta M_{n,B1} + \Delta M_{n,B2} = 0$. If for example $\Delta M_{n,B1} \neq 0$, then Eq. (15) would lead to $$\Delta M_{n,B2} = -\Delta M_{n,B1} - \delta^n \Delta M_{0,B1}, \quad (17)$$

which would require effective gradients in two subsequent encoding blocks to not be related by a simple polarity inversion. Hence, the polarity switching of the gradient vector component $g_i(t)$ in the second encoding block 20 provides a simple and efficient way of minimizing up to an n-th order moment by a first and second encoding block 10, 20 each individually minimizing moments up until only n−1.

The effective gradient vector g(t), and thus also all moments $M_n(t)$, can be arbitrarily rotated as g'(t)=Rg(t), where R is a unitary rotation matrix, to yield arbitrary rotation of tensor b. Note that multidimensional (tensorial) diffusion encoding generally typically involves incoherent gradient waveforms applied along multiple orthogonal directions, i.e. the ratio of gradients along orthogonal direction is not constant. Similarly, vector g(t), and thus also all moments $M_n(t)$, can be arbitrarily scaled as g'(t)=Sg(t), where S is a diagonal matrix, to yield arbitrary shape (eigenvalue ratio) and size (trace) of b. A projection of g(t)' along any direction u is given by [RSg(t)]·u, so if all $M_n(\tau_E) = 0$, also moment projections are zero, [RSg(t)]$M_n(\tau_E)$·u=0.

The desired diffusion weighting gradients might acquire additional undesired components known as concomitant field gradients $g_C(t, r)$, which depend on position relative to the isocenter of the external magnetic field and the external magnetic field density $B_0$. Assuming the external field at isocenter is aligned along the z-axis, concomitant field gradients can be approximated by $$g_C(t, r) \approx G_C(t) r, \quad (18)$$

where $$G_C(t) = \frac{1}{4B_0} \begin{bmatrix} g_z^2(t) & 0 & -2g_x(t)g_z(t) \\ 0 & g_z^2(t) & -2g_y(t)g_z(t) \\ -2g_x(t)g_z(t) & -2g_y(t)g_z(t) & 4g_x^2(t) + 4g_y^2(t) \end{bmatrix} \quad (19)$$

is the concomitant gradient matrix, which depends on the rotation of the gradients and thus also on rotation of the diffusion encoding tensor b. The amount of k-space shift is proportional to $$K = \frac{\gamma}{2\pi} \int_0^{\tau} h(t) G_C(t) dt. \quad (20)$$

To minimize or null the effects of concomitant fields, we require K to be minimized or K=0. This can be achieved for any b-tensor encoding waveforms, provided that the gradients are appropriately rotated relative to the main magnetic field vector $B_0$.

A particular realization of b-tensor encoding with gradient moment nulling (up to arbitrary moment) can be realized when q-trajectory is constrained to be always parallel to one of two stationary orthogonal planes, characterized by normal vectors $n_1$ and $n_2$. Minimizing K or nulling K, so that K=0, can be achieved by applying an appropriate rotation of gradient waveforms.

A number of example effective gradient vector waveforms g(t), designed according to the above will now be discussed.

Figure 2A:
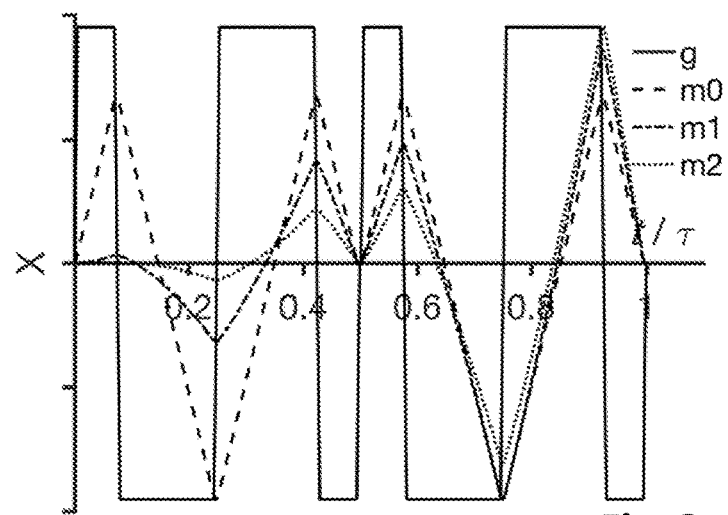
FIG. 2a-c shows example effective diffusion encoding magnetic gradient waveforms and resulting zeroth through second gradient moments.
Figure 2B:
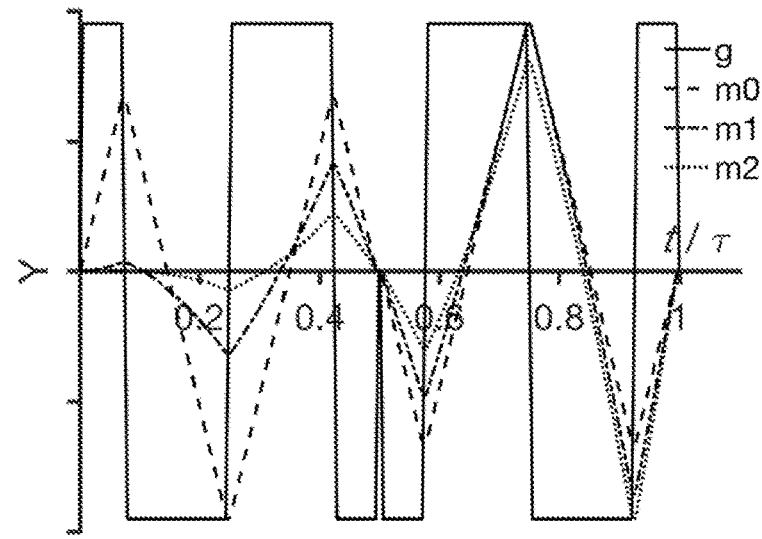
Figure 2C:
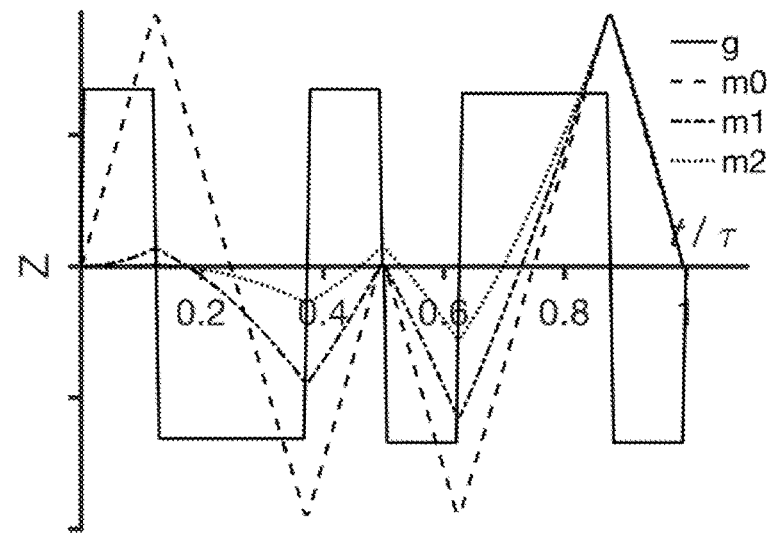

FIG. 2a-c shows in full line effective gradient vector components along axes XYZ. The axes here refer to the axes of the laboratory frame of reference ("XYZ lab-axes"). For simplicity, the start of the first encoding block $\tau_{B1}$ is set to t=0. Additionally, the length of the silent period has been set to zero such that the start of the second encoding block immediately follows the end of the first encoding block t=$\tau_{B1}$. The duration of both encoding blocks is $\tau_B$=0.5. The second encoding block ends at t=$\tau_E$=1. The zeroth order gradient moment "m0", the first order gradient moment "m1", and the second order gradient moment "m2" are indicated by dashed, dashed-dotted and dotted lines respectively, for each axis. The gradient waveform g(t) is velocity (m1) and acceleration compensated (m2). The encoding blocks are sub-divided symmetrically around center of encoding blocks into two sub-intervals (along Z axis) or three sub-intervals (along X and Y axis), so that $$[t'_{1(1)}, t'_{2(1)}] = \left[\frac{1}{4}, \frac{3}{4}\right]\tau_B \text{ and } [t'_{1(1)}, t'_{2(1)}, t'_{3(1)}] = \left[\frac{1}{6}, \frac{3}{6}, \frac{5}{6}\right]\tau_B,$$

respectively. The gradient waveform comprises a number of trapezoidal pulses. More specifically, the X and Y components comprises four trapezoidal pulses in each encoding block whereas the Z component comprises three trapezoidal pulses. As may be seen, for axes X and Y, each one of m0, m1 and m2 become zero at the end of each encoding block (i.e. at t=0.5 and t=1). However, for axis Z only m0 and m1 become zero at the end of the first encoding block while each one of m0, m1 and m2 become zero at the end of the second encoding block. The nulling of m2 at the end of the second encoding block is achieved by the polarity switching of the effective gradient component along the Z axis, visible in FIG. 2c. The gradient amplitudes are adjusted to yield a spherical b-tensor, i.e. achieving isotropic diffusion weighting.

Figure 3A:
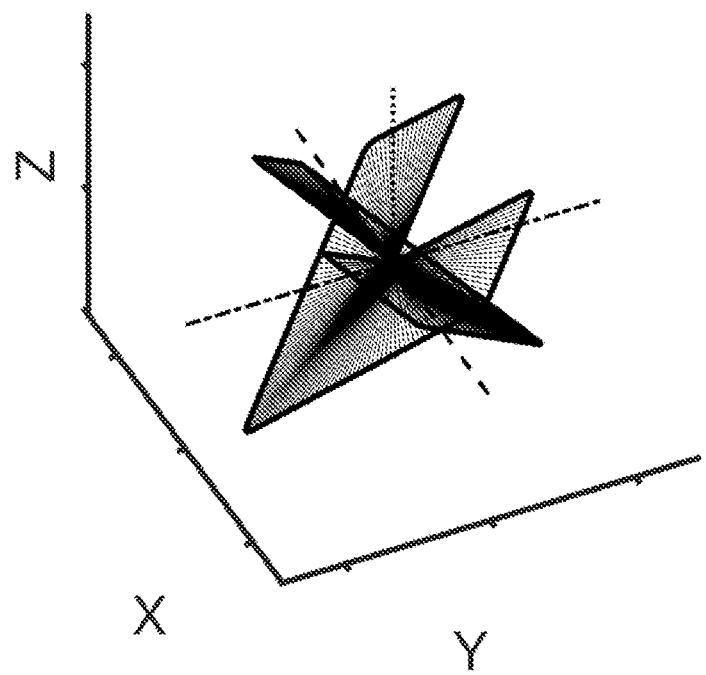
FIG. 3a-b shows q-trajectories for the waveforms of FIG. 2, without and with rotation of gradient waveforms for nulling concomitant field gradients.
Figure 3B:
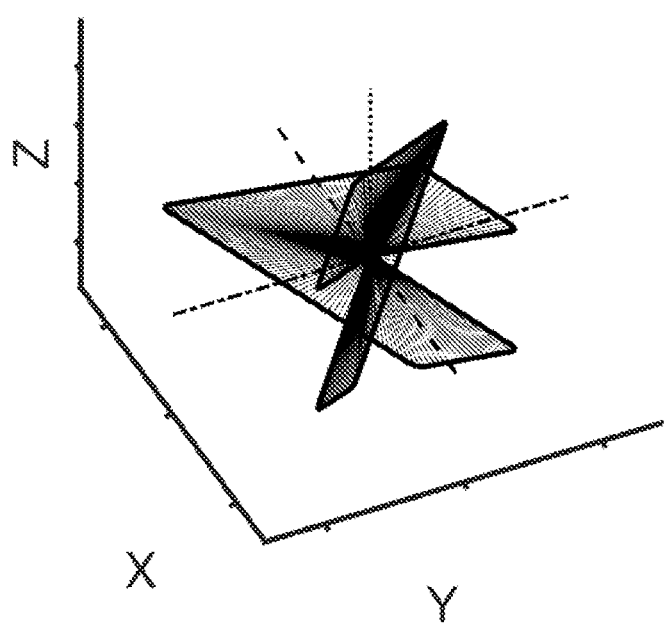

FIG. 3a, b show the q-trajectory for the velocity and acceleration compensated waveforms shown in FIG. 2. FIG. 3a shows the q-trajectory without any rotation for nulling concomitant field gradients. FIG. 3b shows the q-trajectory with rotation for nulling of concomitant field gradients. The dashed, dashed-dotted and dotted lines centered at the q-trajectory show the orientation of the normal to the planes which the q-trajectory is confined to and their cross-product. The shaded areas are shown to ease visualization and is constructed by connecting the origin point to the $M_n(t)$ points.

Figure 4A:
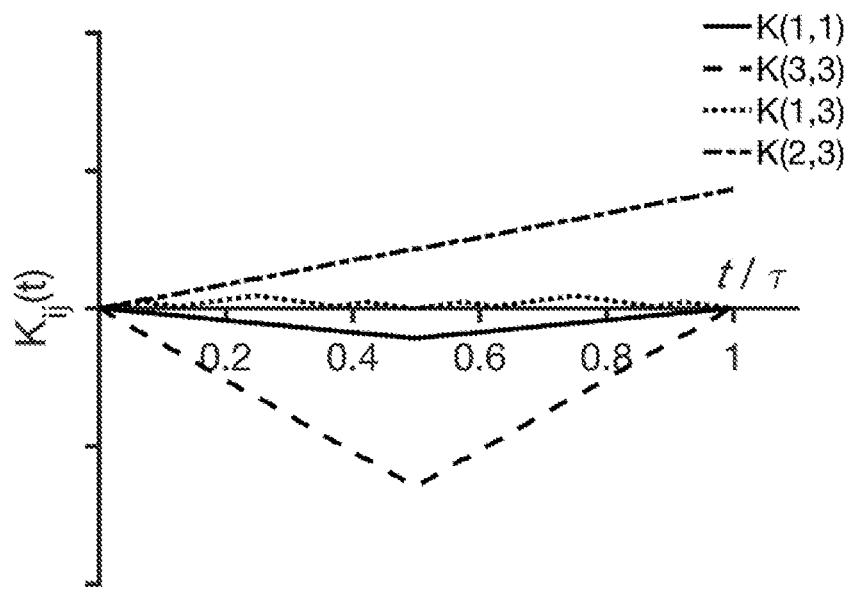
FIG. 4a-b shows the time evolution of the concomitant moment matrix elements $K_{ij}(t)$ for the waveforms shown in FIG. 2, without and with rotation.
Figure 4B:
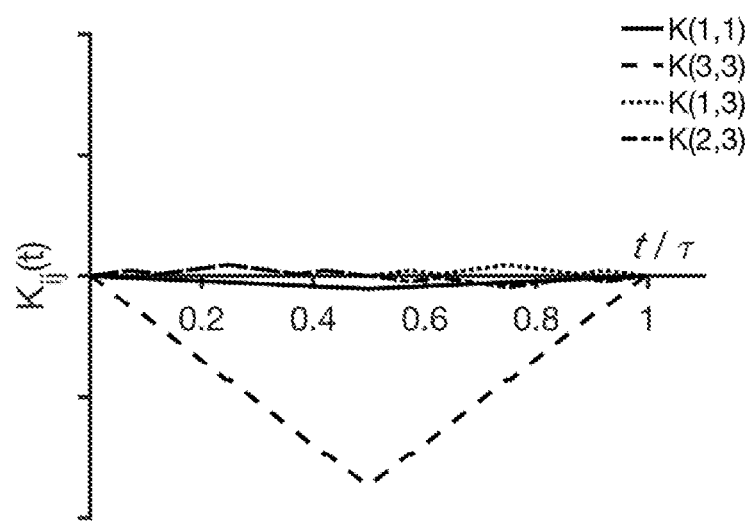

FIGS. 4a, b show the time evolution of the concomitant moment matrix elements $K_{ij}(t)$ for the waveforms shown in FIG. 2, for rotation without (FIG. 4a) and with (FIG. 4b) nulling of concomitant field gradients.

Figure 5A:
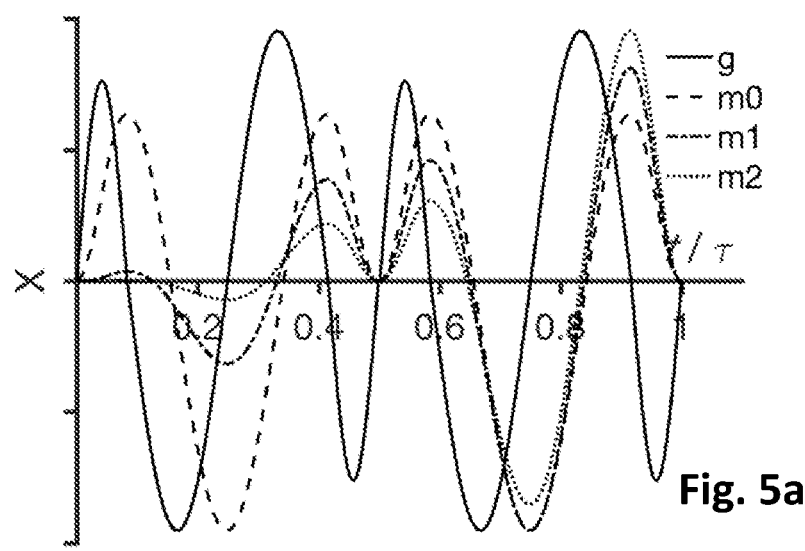
FIG. 5a-c shows further example effective diffusion encoding magnetic gradient waveforms and resulting zeroth through second gradient moments.
Figure 5B:
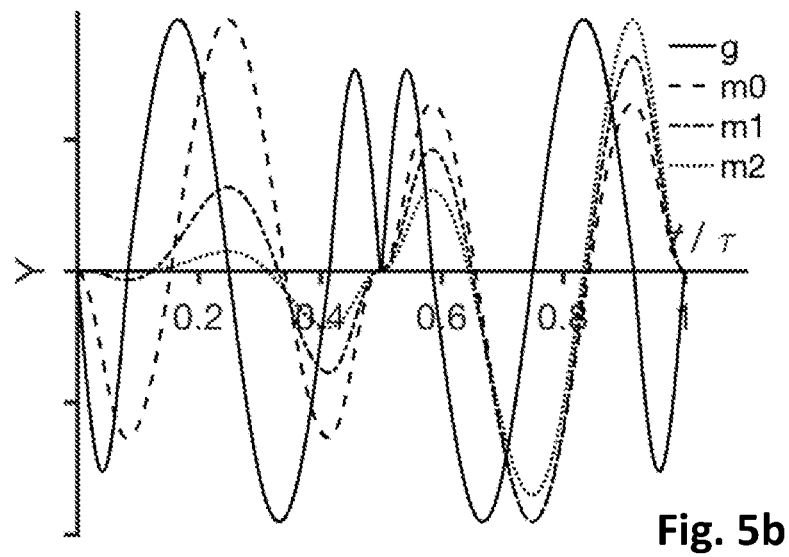
Figure 5C:
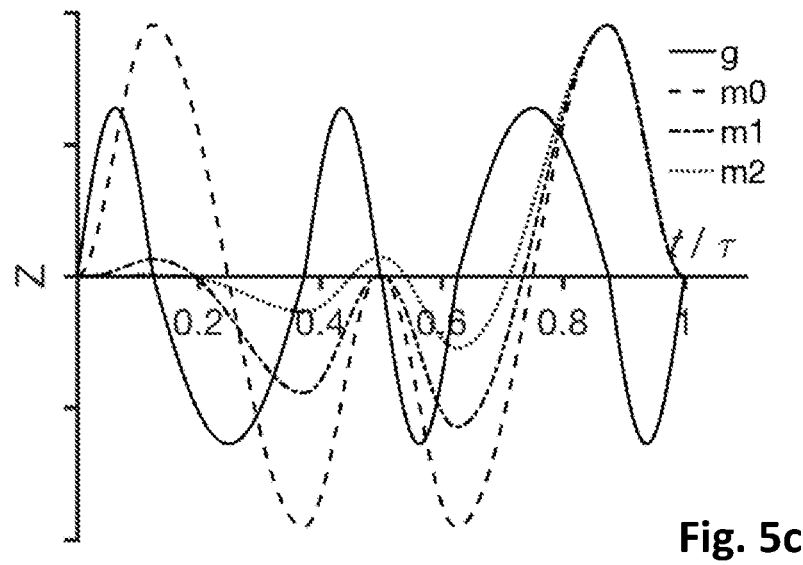

FIG. 5a-c shows in full line effective gradient vector components along axes XYZ. The encoding blocks are sub-divided as in FIG. 2. The waveforms in FIG. 5a-c differ from the waveforms in FIG. 2a-c in that they have a sinusoidal shape. More specifically, the X and Y components comprises four sinusoidal "lobes" in each encoding block whereas the Z component comprises three. As may be seen, for axes X and Y, each one of m0, m1 and m2 become zero at the end of each encoding block (i.e. at t=0.5 and t=1). However, for axis Z only m0 and m1 become zero at the end of the first encoding block while each one of m0, m1 and m2 become zero at the end of the second encoding block. The nulling of m2 at the end of the second encoding block is achieved by the polarity switching of the effective gradient component along the Z axis, visible in FIG. 5c. The gradient amplitudes are adjusted to yield a spherical b-tensor, i.e. achieving isotropic diffusion weighting.

Figure 6:
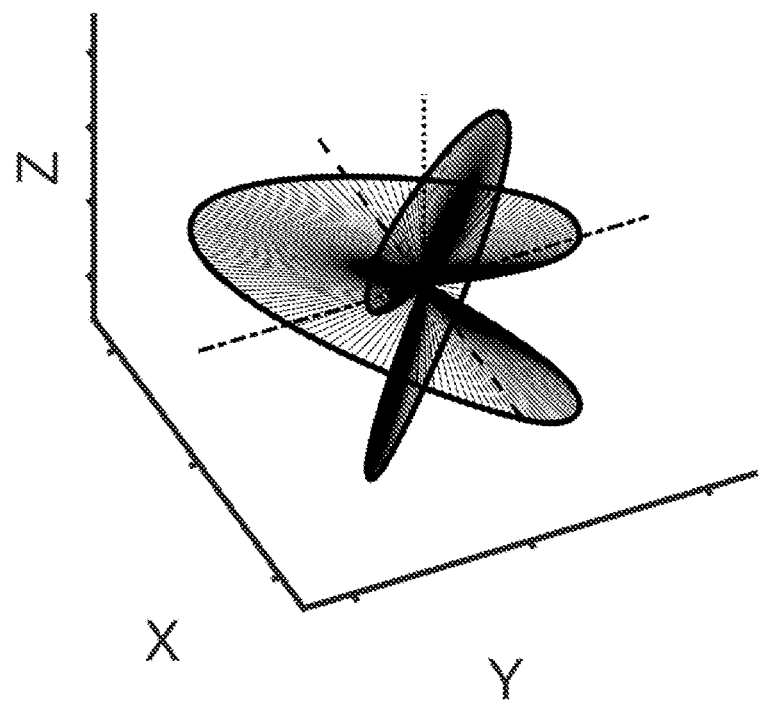
FIG. 6 shows the q-trajectory for the waveforms of FIG. 5 with rotation of gradient waveforms for nulling concomitant field gradients.
Figure 7:
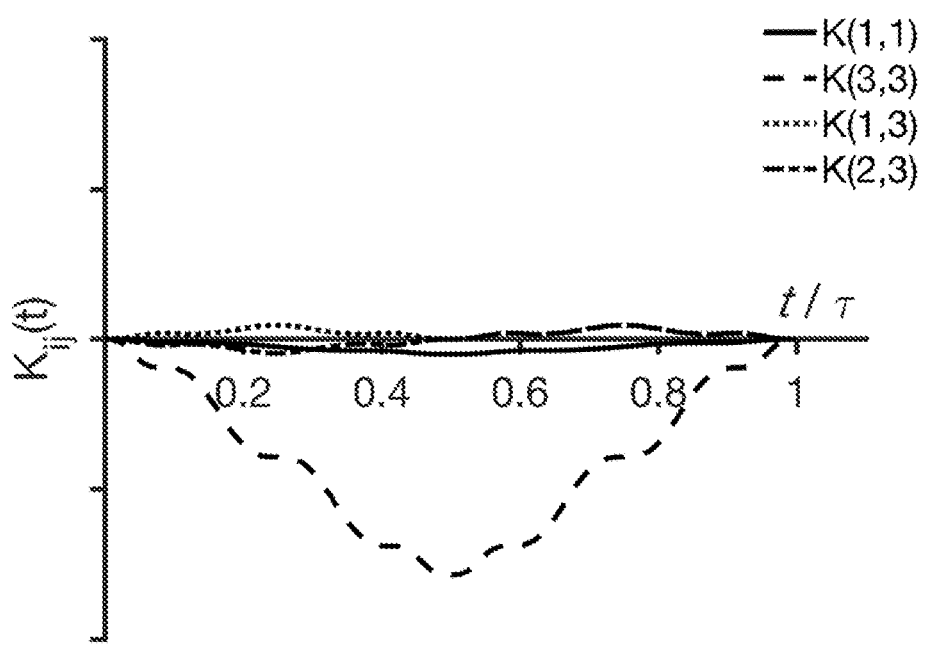
FIG. 7 shows the time evolution of the concomitant moment matrix elements $K_{ij}(t)$ for the waveforms shown in FIG. 5, with rotation.

FIG. 6 shows the q-trajectory and FIG. 7 shows the concomitant moment matrix elements $K_{ij}(t)$ (right) for the velocity and acceleration compensated waveform shown in FIG. 5. As may be seen from FIG. 7, rotation has been applied to achieve concomitant field nulling.

Figure 8A:
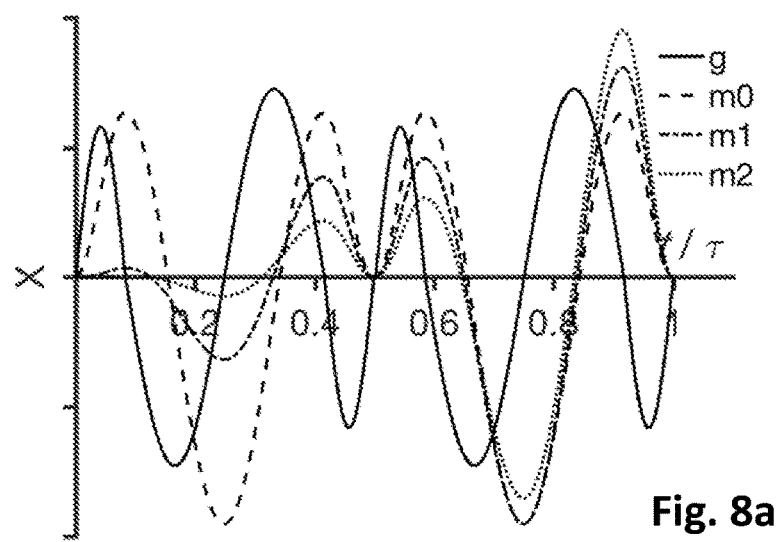
FIG. 8a-c shows further example effective diffusion encoding magnetic gradient waveforms and resulting zeroth through second gradient moments.
Figure 8B:
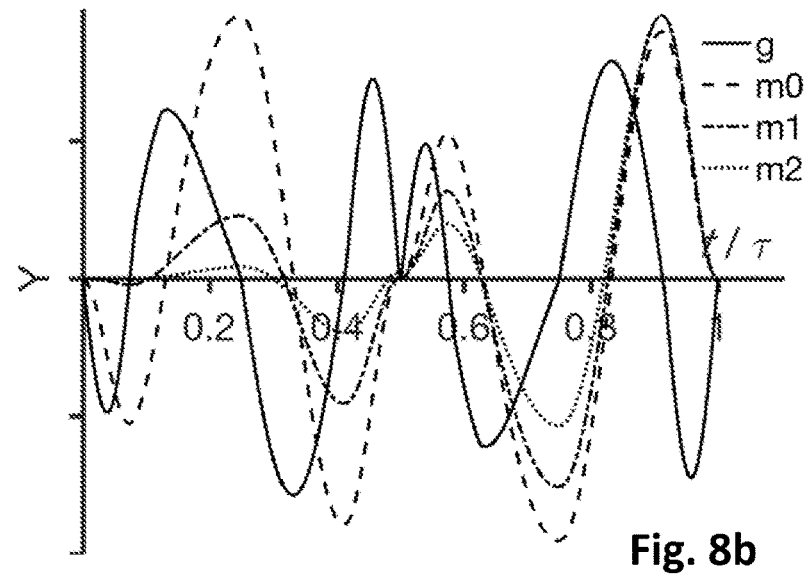
Figure 8C:
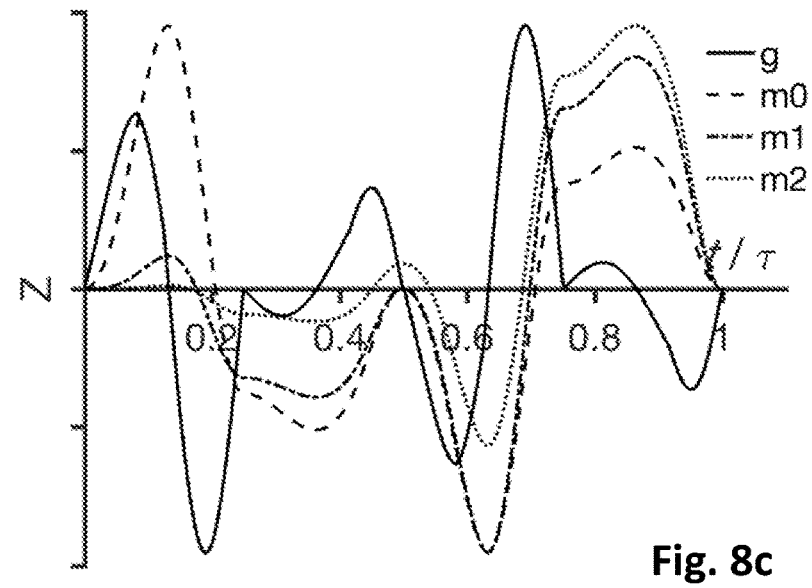

FIG. 8a-c shows in full line effective gradient vector components along axes XYZ. The waveforms have a sinusoidal shape, as the waveforms in FIG. 5. The waveforms in FIG. 8a-c however differ from those in FIG. 5a-c in that the encoding blocks are sub-divided asymmetrically around the center of the encoding blocks into two sub-intervals (along Z axis) or three sub-intervals (along X and Y axis), so that $$[t'_{1(1)}, t'_{2(1)}] = \left[\frac{1}{4}, \frac{2}{4}\right]\tau_B \text{ and } [t'_{1(1)}, t'_{2(1)}, t'_{3(1)}] = \left[\frac{1}{6}, \frac{3}{6}, \frac{5}{6}\right]\tau_B,$$

respectively. As may be seen, for axes X and Y, each one of m0, m1 and m2 become zero at the end of each encoding block (i.e. at t=0.5 and t=1). However, for axis Z only m0 and m1 become zero at the end of the first encoding block while each one of m0, m1 and m2 become zero at the end of the second encoding block. The nulling of m2 at the end of the second encoding block is achieved by the polarity switching of the effective gradient component along the Z axis, visible in FIG. 8c. The gradient amplitudes are adjusted to yield a spherical b-tensor, i.e. achieving isotropic diffusion weighting.

Figure 9:
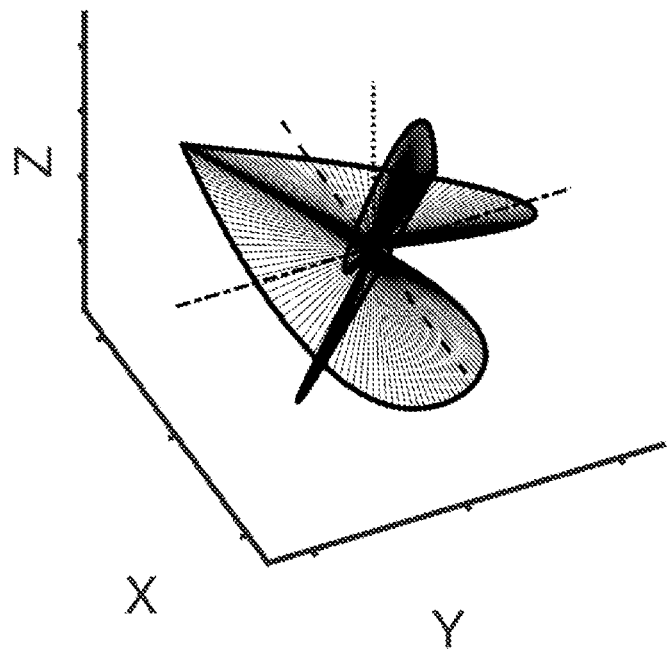
FIG. 9 shows the q-trajectory for the waveforms of FIG. 5.

FIG. 9 shows the q-trajectory for the velocity and acceleration compensated waveform shown in FIG. 8.

Although the gradient amplitudes of the above example waveforms are adjusted to yield spherical b-tensors, it may from the above analysis be understood that the velocity and acceleration compensation may be obtained also for non-spherical b-tensors. Further, although the above examples relate to 3D encoding, velocity and acceleration compensation may also be achieved for 2D encoding, i.e. with a b-tensor comprising only two non-zero eigenvalues.

It should be further be noted that it may be preferred, but not necessary, to enforce the gradient moments to become zero. Rather, one may depending on the measurement requirements establish a threshold $T_n$ for each motion order up to m≥1 which is to be compensated for, the threshold representing a maximum acceptable gradient moment magnitude at the end of the second encoding block $|M_{nl\ (t)}|$.

Accordingly, the condition at the end of the first encoding block may be defined as:

along said direction x: $|M_{nx}(t)| \leq T_n$ for each 0≤n≤m
along said direction y: $|M_{ny}(t)| \leq T_n$ for each 0≤n≤m, and
along said direction z: $|M_{nz}(t)| \leq T_n$ for each 0≤n≤m−1 and $|M_{nz}(t)| > T_n$ for n=m.

The condition at the end of the second encoding block may be defined as:

along each one of the directions l∈(x, y, z): $|M_{nl}(t)| \leq T_n$ for each 0≤n≤m.

Indeed, the waveforms of the above examples meet these conditions assuming thresholds $T_n$ set to 0 or substantially 0.

A similar set of conditions may be established for a 2D encoding scheme.

Figure 10:
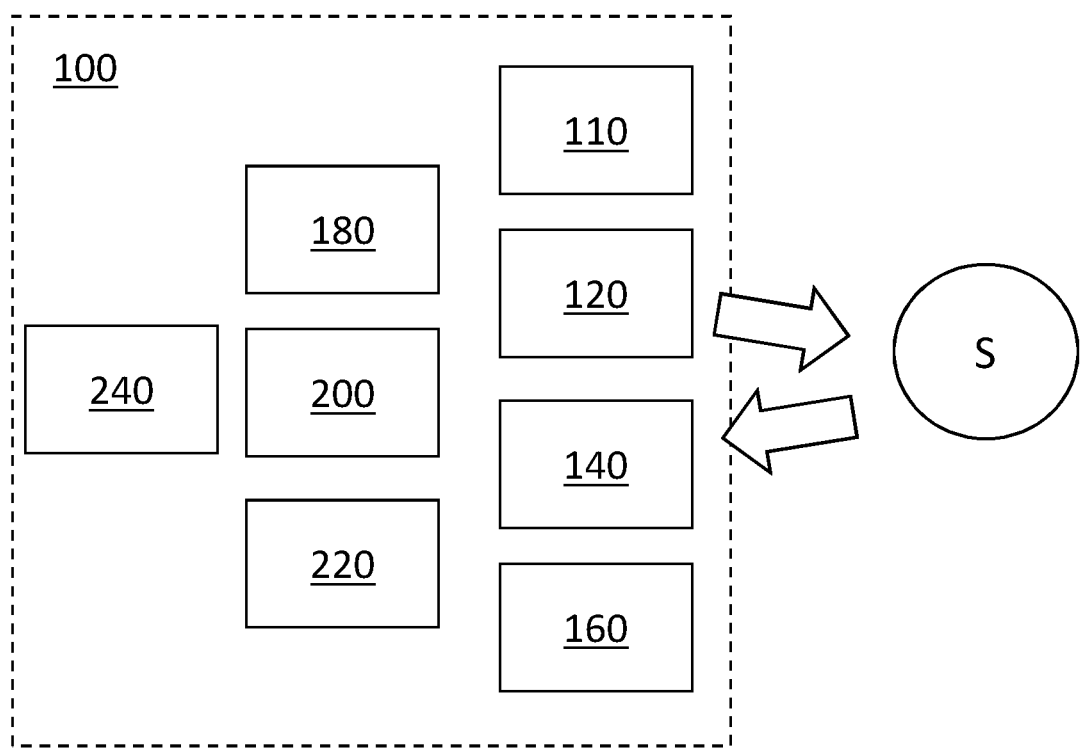
FIG. 10 schematically shows functional blocks of a magnetic resonance scanner.

FIG. 10 shows in a highly schematic manner example functional blocks of a magnetic resonance scanner 100, such as an MRI scanner, which may be operated to perform magnetic resonance measurements on a sample S positioned in the scanner 100. The sample S may for instance correspond to a region-of-interest of a patient, including for instance an organ of the patient such as a heart, kidney or liver. More specifically the scanner 100 may be operated to apply to subject the sample S to a diffusion encoding sequence comprising a diffusion encoding time-dependent magnetic field gradient $g_{lab}(t)$ which together with any RF pulses of the encoding sequence provides an effective gradient $g(t)$ with the above-mentioned properties.

Magnetic gradients may be generated by a gradient coil 120 of the scanner 100. The gradient coil 120 may comprise a coil part for generating each respective component of the gradient $g_{lab}(t)$. The orientation of the gradient $g_{lab}(t)$ may be controlled through the relative orientation of the magnetic gradient components and the static main magnetic field $B_0$ generated by a main magnet 110 of the scanner 100. The scanner 100 may comprise a controller 240 for controlling the operation of the scanner 100, in particular the magnet 110, the gradient coil 120, RF transmission and receiving systems 140, 160 and signal acquisition, etc. The controller 240 may be implemented on one or more processors of the scanner 100 wherein control data for generating the magnetic gradient and RF sequences of the encoding sequence may be implemented using software instructions which may be stored on a computer readable media (e.g. on a non-transitory computer readable storage medium) and be executed by the one or more processors. The software instructions may for example be stored in a program/control section of a memory of the controller 240, to which the one or more processors has access. It is however also possible to implement the functionality of the controller 240 in the form of dedicated circuitry such as in one or more integrated circuits, in one or more application-specific integrated circuits (ASICs) or field-programmable gate arrays (FPGAs), to name a few examples.

As is per se is known in the art, the diffusion encoding magnetic gradients may be supplemented with non-diffusing encoding magnetic gradients (i.e. gradients applied for purposes other than diffusion encoding) such as crusher gradients, gradients for slice selection, imaging correction gradients etc.

The encoding sequence may be followed by a detection block, during the detection block the scanner 100 may be operated to acquire one or more echo signals from the sample S. More specifically, the echo signals may be diffusion attenuated echo signals resulting from the preceding diffusion encoding sequence. The detection block may be implemented using any conventional signal acquisition technique, echo planar imaging (EPI) being one example. The echo signals may be acquired by the RF receiving system 160 of the scanner 100. The acquired echo signals may be sampled and digitized and stored as measurement data in a memory 180 of the scanner 100. The measurement data may for instance be processed by a processing device 200 of the scanner 100. In a dMRI application the processing may for example comprise generating a digital image of the sample S, which for instance may be displayed on a monitor 220 connected to the scanner 100. It is also possible to process acquired echo signals remotely from the scanner 100. The scanner 100 may for instance be configured to communicate with a computer via a communication network such as a LAN/WLAN or via some other serial or parallel communication interface wherein the computer may process received measurement data as desired.

As may be appreciated, an accurate characterization of the sample S, such as by generation of an dMRI image, may be based on echo signal data acquired during a plurality of subsequent measurements, for different strength of diffusion weighting and/or different relative orientations of the static magnetic field and diffusion encoding gradients $g_{lab}(t)$, different shapes and/or dimensionalities of b-tensors etc.

In the above the inventive concept has mainly been described with reference to a limited number of examples. However, as is readily appreciated by a person skilled in the art, other examples than the ones disclosed above are equally possible within the scope of the inventive concept, as defined by the appended claims.

The invention claimed is:

1. A method for performing a diffusion weighted magnetic resonance measurement on a sample, the method comprising:
   operating a magnetic resonance scanner to apply a diffusion encoding sequence to the sample; and
   operating the magnetic resonance scanner to acquire from the sample one or more echo signals;
   wherein the diffusion encoding sequence comprises a diffusion encoding time-dependent magnetic field gradient $g(t)$ with non-zero components $g_l(t)$ along at least two orthogonal directions y and z, and a b-tensor having at least two non-zero eigenvalues, the magnetic field gradient comprising a first and subsequent second encoding block,
   wherein an n-th order gradient moment magnitude along direction $l \in (y, z)$ is given by $|M_{nl}(t)| = |\int_0^t g_l(t') t'^n dt'|$, and the first encoding block is adapted to yield, at an end of the first encoding block:
   along said direction y, $|M_{ny}(t)| \leq T_n$ for each $0 \leq n \leq m$, where $T_n$ is a predetermined n-th order threshold, and
   along said direction z, $|M_{nz}(t)| \leq T_n$ for each $0 \leq n \leq m-1$ and $|M_{nz}(t)| > T_n$ for n=m; and
   the second encoding block is adapted to yield, at an end of the second encoding block:
   along each one of said directions $l \in (y, z)$: $|M_{nl}(t)| \leq T_n$ for each $0 \leq n \leq m$,
   wherein m is an integer order equal to or greater than 1.

2. A method according to claim 1, wherein m is equal to 1.

3. A method according to claim 1, wherein m is equal to or greater than 2.

4. A method according to claim 1, wherein the magnetic field gradient $g(t)$ is adapted to present:
   between a start of the first encoding block and the end of the first encoding block: m+1 zero crossings along said direction y and m zero crossings along said direction z, and
   between a start of the second encoding block and the end of the second encoding block: m+1 zero crossings along said direction y and m zero crossings along said direction z.

5. A method according to claim 1, wherein the first and second encoding blocks are of a duration $\tau_B$ and begin at time $t_{B1}$ and $t_{B2}$, respectively, and wherein $$g_y(t_{B1}+t') = \pm g_y(t_{B2}+t'), \text{ and}$$

$$g_z(t_{B1}+t') = -g_z(t_{B2}+t'),$$

for $0 \leq t' \leq \tau_B$.

6. A method according to claim 1, wherein the magnetic field gradient comprises a silent block between the first and second encoding blocks during which g(t) is zero, and wherein the diffusion encoding sequence further comprises at least one radio frequency pulse applied to the sample during the silent block.

7. A method according to claim 1, wherein the b-tensor has exactly two non-zero eigenvalues.

8. A method according to claim 1, wherein the b-tensor has exactly three non-zero eigenvalues and the magnetic field gradient g(t) has non-zero components $g_i(t)$ along three orthogonal directions x, y and z, and wherein:
the first encoding block is further adapted to yield, at the end of the first encoding block:
along said direction x, $|M_{nx}(t)| \leq T_n$ for each $0 \leq n \leq m$, and
the second encoding block is further adapted to yield, at the end of the second encoding block:
along said direction x: $|M_{nx}(t)| \leq T_n$ for each $0 \leq n \leq m$.

9. A method according to claim 8, wherein the magnetic field gradient g(t) is adapted to present:
between a start of the first encoding block and the end of the first encoding block: m+1 zero crossings along each of said directions x and y and m zero crossings along said direction z, and
between a start of the second encoding block and the end of the second encoding block: m+1 zero crossings along each of said directions x and y and m zero crossings along said direction z.

10. A method according to claim 8, wherein the first and second encoding blocks are of a duration $T_B$ and begin at time $t_{B1}$ and $t_{B2}$, respectively, and wherein $g_x(t_{B1}+t')=g_x(t_{B2}+t')$, $g_y(t_{B1}+t')=-g_y(t_{B2}+t')$, and $g_z(t_{B1}+t')=-g_z(t_{B2}+t')$, for $0 \leq t' \leq \tau_B$.

11. A method according to claim 8, wherein a trajectory of a dephasing vector $q(t)=\gamma \int_0^t g(t')dt'$ is confined to two orthogonal planes during the magnetic field gradient g(t).

12. A method according to claim 8, wherein the diffusion encoding sequence is adapted to cause isotropic diffusion encoding in the sample.

13. A method according to claim 8, wherein the sample is arranged in a static magnetic field $B_0=(0, 0, B_0)$ oriented along said direction z, and wherein the magnetic field gradient g(t) is oriented with respect to static magnetic field such that $$K = \frac{\gamma}{2\pi} \int_0^{\tau_E} h(t') G_C(t') dt' \text{ is zero, where}$$

$$G_C(t) = \frac{1}{4B_0} \begin{bmatrix} g_z^2(t) & 0 & -2g_x(t)g_z(t) \\ 0 & g_z^2(t) & -2g_y(t)g_z(t) \\ -2g_x(t)g_z(t) & -2g_y(t)g_z(t) & 4g_x^2(t)+4g_y^2(t) \end{bmatrix}.$$

14. A method according to claim 1, further comprising processing, by a processing device, data representing the one or more echo signals acquired from the sample to generate an image of the sample.

* * * * *